US010323112B2

(12) United States Patent
Atkins et al.

(10) Patent No.: US 10,323,112 B2
(45) Date of Patent: Jun. 18, 2019

(54) FLUORESCENT MONOMERS AND TAGGED TREATMENT POLYMERS CONTAINING SAME FOR USE IN INDUSTRIAL WATER SYSTEMS

(71) Applicant: ECOLAB USA INC., St. Paul, MN (US)

(72) Inventors: Jeffery M. Atkins, Aurora, IL (US); Barbara E. Moriarty, Palatine, IL (US); Paul J. Zinn, Oswego, IL (US)

(73) Assignee: ECOLAB USA INC., St. Paul, MN (US)

( * ) Notice: Subject to any disclaimer, the term of this patent is extended or adjusted under 35 U.S.C. 154(b) by 16 days.

(21) Appl. No.: 15/602,349

(22) Filed: May 23, 2017

(65) Prior Publication Data
US 2017/0260076 A1 Sep. 14, 2017

Related U.S. Application Data

(62) Division of application No. 13/730,087, filed on Dec. 28, 2012, now Pat. No. 9,751,789.

(51) Int. Cl.
| *C08F 212/32* | (2006.01) |
| *C08F 12/32* | (2006.01) |
| *C09B 57/08* | (2006.01) |
| *C09B 69/10* | (2006.01) |
| *C02F 5/12* | (2006.01) |
| *C09K 11/06* | (2006.01) |
| *C07D 491/06* | (2006.01) |
| *C02F 103/32* | (2006.01) |
| *C02F 103/28* | (2006.01) |
| *C02F 103/16* | (2006.01) |
| *C02F 103/10* | (2006.01) |
| *C02F 103/02* | (2006.01) |
| *C02F 1/00* | (2006.01) |

(52) U.S. Cl.
CPC .............. *C08F 212/32* (2013.01); *C02F 5/12* (2013.01); *C07D 491/06* (2013.01); *C08F 12/32* (2013.01); *C09B 57/08* (2013.01); *C09B 69/109* (2013.01); *C09K 11/06* (2013.01); *C02F 1/008* (2013.01); *C02F 2103/023* (2013.01); *C02F 2103/10* (2013.01); *C02F 2103/16* (2013.01); *C02F 2103/28* (2013.01); *C02F 2103/32* (2013.01)

(58) Field of Classification Search
CPC .. C07D 471/06; C07D 487/06; C07D 495/06; C07D 513/06
See application file for complete search history.

(56) References Cited

U.S. PATENT DOCUMENTS

| 3,367,937 A | 2/1968 | Fuchs et al. |
| 3,748,330 A | 7/1973 | Fuchs et al. |
| 3,888,862 A | 6/1975 | Meininger et al. |
| 3,888,863 A | 6/1975 | Troster |
| 6,001,936 A * | 12/1999 | Barrera .................. C08F 283/00 525/454 |
| 6,645,428 B1 | 11/2003 | Morris et al. |
| 6,894,105 B2 * | 5/2005 | Parent .................... C08F 246/00 428/421 |
| 7,087,677 B2 | 8/2006 | Kaul et al. |
| 7,601,789 B2 | 10/2009 | Morris et al. |
| 2004/0016370 A1* | 1/2004 | Olson ..................... C09B 23/02 106/498 |
| 2004/0063889 A1* | 4/2004 | Kaul .................... C07D 495/06 526/328.5 |
| 2005/0242042 A1 | 11/2005 | Moriarty et al. |
| 2006/0111367 A1* | 5/2006 | Qian .................... C07D 221/14 514/253.02 |
| 2006/0160226 A1 | 7/2006 | Johnson |
| 2008/0234287 A1 | 9/2008 | Qian et al. |

FOREIGN PATENT DOCUMENTS

| GB | 1345176 A | 1/1974 | |
| GB | 1518855 A * | 7/1978 | ............. C09B 57/14 |
| GB | 1518855 A | 7/1978 | |
| JP | 2003-531283 A | 10/2003 | |
| JP | 2007-535402 A | 12/2007 | |
| JP | 2008-533438 A | 8/2008 | |
| WO | WO 01/81654 A1 | 11/2001 | |
| WO | WO 2005/110925 A2 | 11/2005 | |
| WO | WO 2008/001036 A2 | 1/2008 | |
| WO | WO-2008001036 A2 * | 1/2008 | ............. C09B 57/08 |

OTHER PUBLICATIONS

International Search Report and Written Opinion for corresponding International Application No. PCT/US2013/075456, 10 pages (dated Apr. 28, 2014).
Supplementary European Search Report for corresponding European Application No. 13869152.2, 2 pages (dated May 31, 2016).
European Search Report for related European Application No. 17184191.9, 2 pages (dated Dec. 6, 2017).

* cited by examiner

*Primary Examiner* — Clare M Perrin
(74) *Attorney, Agent, or Firm* — Eric D. Babych; Brinks Gilson & Lione

(57) ABSTRACT

The present disclosure relates to methods and compositions for making and using fluorescent monomers which are synthesized by reacting a substituted or non-substituted benzoxanthene anhydride with an amine and with a moiety containing a polymerizable group. Such monomers are useful for the preparation of tagged treatment polymers. Such tagged treatment polymers are useful as scale inhibitors in industrial water systems.

20 Claims, No Drawings

FLUORESCENT MONOMERS AND TAGGED TREATMENT POLYMERS CONTAINING SAME FOR USE IN INDUSTRIAL WATER SYSTEMS

TECHNICAL FIELD

The present invention relates generally to fluorescent monomers. In another aspect, this invention relates to tagged treatment polymers that contain these fluorescent monomers. In a further aspect, this invention relates to the use of tagged treatment polymers containing fluorescent monomer(s) therein in industrial water systems.

BACKGROUND

In many industrial water systems that employ polymers as water treatment agents it may be desirable to tag or mark such polymers to facilitate monitoring thereof. By the term "monitoring" is meant herein any type of tracing or tracking to determine the location or route of the polymers, and any type of determination of the concentration or amount of the polymer at any given site, including singular or intermittent or continuous monitoring. For instance, it may be desirable to monitor water treatment polymers in water systems, or to monitor polymers that may be present in waste fluids before disposal, or to monitor the polymer used in fluids for down-hole oil well applications, or to monitor polymers that may be present in fluids used to wash a manufactured product.

As seen from the above list of possible applications of polymer monitoring, the purpose of such monitoring may be to trace or track or determine the level of the polymer itself, or to trace or track or determine the level of some substance in association with the polymer, or to determine some property of the polymer or substance in association with the polymer, for instance its leachability.

There are many industrial water systems. Because water resources are becoming limited and efficient utilization of water is required, various methods have been adopted to reduce the amount of water used in all industrial water systems. As the methods for reducing the amount of water are put into practice, unfavorable events can occur. These unfavorable events occur because the quality of the water in the system is progressively deteriorated. These unfavorable events can include the formation of scale.

To prevent or minimize unfavorable events, various kinds of treatment agents for treatment of water systems have been used. It has been found that organic substances, including certain types of treatment polymers, are effective for preventing formation of scale. These certain types of treatment polymers are known to persons of ordinary skill in the art of industrial water treatment and are widely used by themselves or as one of many possible components in scale inhibition products.

When a treatment polymer is used for preventing formation of scale the concentration of the treatment polymer in the water system is the important factor so that the treatment polymer performs the desired function with good efficiency. For example, a treatment polymer added to a cooling water system can be consumed by many causes. With consumption, the amount of the treatment polymer dissolved in the cooling water does not remain the same as the amount added to the cooling water. Therefore, it is important for the optimum operation of an industrial water system that practical methods are known to determine the concentration of treatment polymers in the water of the industrial water system.

In general practice, the amount of the treatment polymer added to the water in an industrial water system can be measured using various analytical methods. The use of an inert fluorescent tracer or mass balance measurement method as described in U.S. Pat. Nos. 4,783,314; 4,992,380; and 5,171,450, hereby incorporated by reference; to perform this analysis is known in the art.

In the inert fluorescent tracer method, an inert fluorescent tracer is added to an industrial water system, with the amount of inert fluorescent tracer added being proportional to the amount of the treatment polymer added. By using a fluorometer to measure the fluorescent signal of the inert fluorescent tracer, the amount of the inert fluorescent tracer can be determined by using a calibration curve to relate the amount of fluorescent signal detected to the amount of the inert fluorescent tracer present. Because the inert fluorescent tracer and the treatment polymer are added to the industrial water system in known proportions, by knowing the amount of inert fluorescent tracer present it also means that the amount of treatment polymer present is known.

The inert fluorescent tracer method can be conducted on-line and in real time so that any changes in the amount of treatment polymer being added to the system can be made immediately. As a complement to the use of an inert tracer system, it has been found that treatment polymers that are used as components of scale inhibitors in industrial water systems could be monitored if tagged with a fluorescent monomer. The amount of fluorescent monomer incorporated into the tagged treatment polymer must be enough so that the fluorescence of the tagged treatment polymer can be adequately measured; however, it must not be so much that the performance of the tagged treatment polymer as a treatment agent for the water is decreased. Because the concentration of the tagged treatment polymer itself can be determined using a fluorometer, it is now possible to measure consumption of the tagged treatment polymer directly. It is important to be able to measure consumption directly because consumption of a treatment polymer usually indicates that a non-desired event, such as scaling, is occurring. Thus, by being able to measure consumption of the tagged treatment polymer, there can be achieved an on-line, real time, in-situ measurement of scaling activity in the cooling system.

There are a number of florescence measuring processes and tagged polymer process known in the art. Some examples are described in U.S. Pat. Nos.: 5,986,030, 6,312, 644, 6,645,428, 7,148,351, 7,601,789, 7,875,720, 6,358,746, 3,888,863, 3,310,564, 3,845,075, and 4,377,703, International Published Patent Applications: WO 2011/036075 A1 and WO2008/001036 A2, Canadian Patent Document CA 884330 A, United Kingdom Patent Documents: GB 1,378, 880, GB 1,518,855, GB 1,392,253, GB 1,384,821, GB 1,095,784, GB 1,345,176 and scientific papers: *Synthesis of a Novel Oxoxanthenoisoquinoline via a Palladium-Catalysed Cross-Coupling Reaction; as a Fluorophore*, by Mark P Prickett et al., Tetrahedron Letters, Vol. 41, Issue 16, pp. 2987-2990 (2000) and *Benzo[k, l], Xanthene-3,4-Dicarboximides and Benzimidazoxanthenoisoquinolinones—Yellow and Orange Dyes for Synthetic-Polymer Fibres*, by A T Peters et al., Journal of the Society of Dyers and Colourists, Vol. 105, Issue 1, pp. 29-35 (1989). However, there are few viable tagged treatment polymers for use as treatment polymers in industrial water systems. Therefore, it is desirable to produce additional tagged treatment polymers that have a fluorescent signal so that a fluorometer can be used to measure the fluorescent signal of the tagged treatment polymer and determine the concentration of tagged treatment polymer currently present in the industrial water system from that information.

It is known that tagging of polymers is difficult to accomplish because of the difficulty in chemically combining fluorescent moieties with non-fluorescent polymers. Therefore, in order to synthesize tagged treatment polymers it is also desirable to produce fluorescent monomers that are readily polymerized to form tagged treatment polymers.

Thus it is clear that there is definite utility in novel methods and compositions for making and using tagged treatment polymers. The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR § 1.56(a) exists.

BRIEF SUMMARY

At least one embodiment of the invention is directed towards novel monomers, novel polymers made from those monomers, and novel methods of their use as tagged polymers.

At least one embodiment of the invention is directed towards a method of maintaining a desired amount of tagged treatment polymer in an industrial water system comprising the steps of: a) adding an inert tracer and a tagged treatment polymer to the water of an industrial water system, such that a desired concentration of said tagged treatment polymer is present in said water, b) using a fluorometer to detect the fluorescent signals of said inert tracer and said tagged treatment polymer, c) converting the fluorescent signals of said inert tracer and said tagged treatment polymer to the concentration of said inert tracer and said tagged treatment polymer, and d) adjusting the concentration of said tagged treatment polymer according to what the desired concentration is for said tagged treatment polymer in said industrial water system.

The tagged treatment polymer may be selected from the group consisting of: $G_aQ_jW_t$, $G_a Q_v W_f S_c$, and any combination thereof. G, Q, W and S may all be monomeric units (a polymer is a chain of chemically bonded monomeric units) making up a backbone of a polymer chain. G is the tag and Q, W, and S are other monomeric units. The distribution of G, Q, W and S along the polymer chain are in random order and in relative amounts of a, j, t, v, f, and c. For polymer $G_a Q_v W_f S_c$ a may be from about 0.001 to about 10.00 mole percent; v may be from about 0 to about 97.999 mole percent; f may be from about 1 to about 97.999 mole percent; c may be from about 1 to about 40 mole percent; and a+v+f+c=100. For polymer $G_aQ_jW_t$ a may be from about 0.001 to about 10.0 mole percent; j may be from about 0 to about 99.999 mole percent; t may be from about 0 to about 99.999 mole percent; and a+j+t=100.

The polymer may be a tripolymer, a terpolymer, or any other sort of copolymer made up of multiple kinds of monomeric units.

G may be selected from the group consisting of Formula I, Formula II,

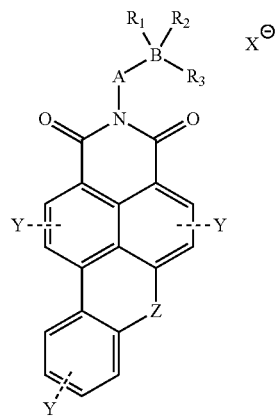

Formula I

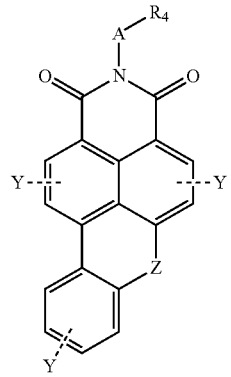

Formula II

In Formula I: Y may be one or more of the following: H, F, Cl, Br, $NO_2$, $CO_2H$ and its salts, $PO_3H_2$ and it salts, $SO_3H$ and its salts, $SO_2NH_2$ or $SO_2NR_2$; Z may be one of the following: $CH_2$, C=O, $CR_2$, NH, NR, $NH_2^+$, $NR_2^+$, NOH, O, S, SO, or $SO_2$; $R_1$ and $R_2$ may be alkyl; $R_3$ may be selected from the group consisting of allyl, 2-hydroxy-3-allyloxy-propyl, vinyl benzyl, 3-methacrylamidopropyl, 3-acrylamidopropyl, 2-acryloxyethyl and 2-methacryloxyethyl. A may be selected from the group consisting of alkyl, alkyloxyalkyl, alkylamidoalkyl, aryl or nonexistent; with the proviso that when A is nonexistent, B is nitrogen (N) and B is bonded directly to the imide nitrogen. B may be sulfur or nitrogen with the proviso that when B is sulfur only one of $R_1$ or $R_2$ is present. X may be an anionic counter ion.

In Formula II: Y may be one or more of the following: H, F, Cl, Br, $NO_2$, $CO_2H$ and its salts, $PO_3H_2$ and it salts, $SO_3H$ and its salts, $SO_2NH_2$ or $SO_2NR_2$; Z may be one of the following: $CH_2$, C=O, $CR_2$, NH, NR, $NH_2^+$, $NR_2^+$, NOH, O, S, SO, or $SO_2$; A may be selected from the group consisting of alkyl, alkyloxyalkyl, alkoxy, alkylamidoalkyl, alkylamino, NH, aryl or nonexistent; $R_4$ is selected from the group consisting of allyl, acryl, methacryl, 2-hydroxy-3-allyloxy-propyl, vinyl benzyl, 2-acryloxyethyl and 2-methacryloxyethyl.

Q may be selected from the group consisting of acrylic acid and salts thereof, methacrylic acid and salts thereof, maleic acid and salts thereof, maleic anhydride, acrylamide, crotonic acid, acrylamidomethylpropane sulfonic acid and salts thereof; and Q cannot be the same as W.

S may be selected from the group consisting of sulfomethylacrylamide and sulfoethylacrylamide.

W may be selected from the group consisting of: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, diallylamine, acid salts of diallylamine, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, and N-vinylpyrrolidone.

DETAILED DESCRIPTION

The following definitions are provided to determine how terms used in this application, and in particular how the claims, are to be construed. The organization of the definitions is for convenience only and is not intended to limit any of the definitions to any particular category. "Aldrich" means Aldrich Chemical Company, P.O. Box 2060, Milwaukee, Wis. 53201 USA, Telephone Numbers (414) 273-3850 and (800) 558-9160;

"Aliphatic Amine" refers to amines in which the amine group is attached to a saturated carbon atom;

"Alkoxy" means a moiety of the formula RO—, where R is alkyl;

"Alkoxylalkyl" means a moiety of the formula R—O—$R_1$, where R and $R_1$ are alkyl;

"Alkylamidoalkyl" means a moiety of the formula R—C(O)NH—$R_1$—, where R and $R_1$ are alkyl;

"Alkylamino" means a moiety of the formula R—NH—, where R is alkyl;

"Alkyl", whenever it is used, means a fully saturated hydrocarbon moiety with from 1 to 10 carbon atoms;

"Allyl" means a moiety of the formula —$CH_2CH$=$CH_2$;

"Anionic Counter Ion" means an organic or inorganic ion that bears a negative charge to counterbalance the positive charge present on the monomer. Examples include, but are not limited to chloride, sulfate, acetate, methylsulfate, hydroxide and bromide;

"Aryl" means a moiety of the formula Ar—, where Ar is an aromatic unit;

"Benzoxanthene" means a moiety of the formula:

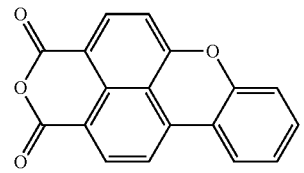 [SMILES: O=c1oc(=O)c2ccc3c4ccccc4oc4ccc1c2c43]

"Branching Agent" means a "Cross-Linking Agent" that is administered at a low level (less than 0.05 weight percent based on the weight of the polymer). It is understood that Branching Agents are added to form "branches" not cross-links;

"Carboxylate" means a moiety of —C(O)OM, where M is H, Na or another cationic counter ion;

"Chain Transfer Agent" means any molecule, used in free-radical polymerization, which will react with a polymer radical forming a dead polymer and a new radical. Representative Chain Transfer Agents are listed by K. C. Berger and G. Brandrup, "*Transfer Constants to Monomer, Polymer, Catalyst, Solvent, and Additive in Free Radical Polymerization,*" Section II, pp. 81-151, in "*Polymer Handbook,*" edited by J. Brandrup and E. H. Immergut, 3d edition, 1989, John Wiley & Sons, New York.

"Cross-Linking Agent" means a composition of matter which chemically links two distinct polymer chains, such as a composition that links an ethylenically unsaturated monomer either containing at least two sites of ethylenic unsaturation or containing one site of ethylenic unsaturation and one site of a reactive group such as an epoxide or an aldehyde. A Cross-Linking Agent may be added to branch or increase the molecular weight of the tagged treatment polymer of this invention. Representative Cross-Linking Agents include N,N-methylenebisacrylamide, N,N-methylenebismethacrylamide, polyethylene glycol diacrylate, ethylene glycol dimethacrylate, diethylene glycol dimethacrylate, triethylene glycol dimethacrylate, polyethylene glycol dimethacrylate, polypropylene glycol dimethacrylate, N-vinyl acrylamide, divinyl benzene, triallyl ammonium salts, N-methyl allylacrylamide, glycidyl acrylate, acrolein, methylolacrylamide, glyoxal, epichlorohydrin, and the like. The crosslinker may be added at from about 0.0001 to about 10, preferably from about 0.0001 to about 0.2 weight percent based on the weight of the polymer;

"Dialkylamino" means a moiety of the formula $R_{21}$—N—$R_{22}$, where $R_{21}$ and $R_{22}$ are alkyl;

"Halogen" means a moiety selected from the group consisting of F, Cl, Br, and I;

"HLB" means the hydrophillic-lipophillic balance of a composition which is a measure of the degree to which it is hydrophilic or lipophilic, it can be determined by the equation:

HLB=20*Mh/M in which Mh is the molecular mass of the hydrophilic portion of the Molecule, and M is the molecular mass of the whole molecule, giving a result on a scale of 0 to 20. An HLB value of 0 corresponds to a completely lipidphilic/hydrophobic molecule, and a value of 20 corresponds to a completely hydrophilic/lipidphilic molecule. HLB values are characterized as:
HLB<10: Lipid soluble (water insoluble)
HLB>10: Water soluble (lipid insoluble)
HLB from 4 to 8 indicates an anti-foaming agent
HLB from 7 to 11 indicates a W/O (water in oil) emulsifier HLB from 12 to 16 indicates O/W (oil in water) emulsifier
HLB from 11 to 14 indicates a wetting agent
HLB from 12 to 15 indicates a detergent
HLB of 16 to 20 indicates a solubiliser or hydrotrope.

"Hydroxyalkyl" means a moiety where an —OH group is attached to an alkyl group;

"Spectrometry" and "Spectroscopy" means the process of analyzing the interaction between a sample of matter and electromagnetic radiation to determine one or more physical properties of the sample of matter. Forms of electromagnetic radiation used include but are not limited to one or more of microwave, terawave, infrared, near infrared, visible, ultraviolet, x-ray, radiation. The analysis includes measurements of one or more of the radiation's absorption, emission, fluorescence, colorometrics, color changes, reflection, scattering, impedance, refraction, and resonance by the sample of matter.

"Substituted Aliphatic Amine" means amines in which the amine group is attached to a saturated carbon of an organic molecule which may bear functional groups such as hydroxyl, carboxyl, etc.;

"Surfactant" is a broad term which includes anionic, nonionic, cationic, and zwitterionic surfactants. Enabling descriptions of surfactants are stated in *Kirk-Othmer, Encyclopedia of Chemical Technology*, Third Edition, volume 8, pages 900-912, and in *McCutcheon's Emulsifiers and Detergents*, both of which are incorporated herein by reference.

"Vinyl" means a moiety which has a carbon-carbon double bond;

"Vinylbenzyl" means a moiety of the formula;

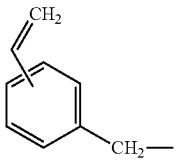

"Vinylbenzyloxy" means a moiety of the formula:

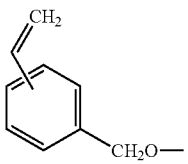

"Water Soluble" means materials that are soluble in water to at least 3%, by weight, at 25 degrees C.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

In at least one embodiment of the invention one or more fluorescent monomers is useful in the preparation of tagged treatment polymers containing same, with said tagged treatment polymers in turn being able to provide a means for achieving better monitoring in industrial water systems.

In at least one embodiment a fluorophore is used using a benzoxanthene moiety. It has an advantageous spectral profile with respect to standard background fluorescence interference, leading to improved signal detection. It can also be incorporated within a water-soluble polymer in lower loading levels than prior art tagging materials.

While benzoxanthenes have been used as fluorescent dyes for textiles and HDPE polymers, the prior art does not contemplate the use of the benzoxanthene fluorophore as a fluorescent tag for water soluble polymers. Moreover these tags display a number of unexpected results. The benzoxanthene fluorophore has greater intensity and better halogen stability than current tags. In addition, it has better stability in light compared to the current tagged polymer via fluorescence. A sulfonated benzoxanthene structure has improved water solubility, whereas the unsulfonated benzoxanthene is oil soluble. This also means that the benzoxanthene can be incorporated within a water-soluble polymer in lower loading levels than current tags. The benzoxanthene fluorophore has an advantageous spectral profile with respect to standard background fluorescence in cooling tower waters.

An advantage of the fluorescent monomers of this invention is that in their use in the formation of a tagged treatment polymer, the fluorescent monomer is not significantly affected by other structures in the polymer or by other ingredients in the system. Thus, the polymers are stable in the presence of oxidizing biocides containing chlorine and or bromine, available from Nalco an Ecolab Company, 1601 West Diehl Rd, Naperville, Ill. 60563.

A further advantage of the tagged treatment polymers of this invention is that the spectral properties, i.e. both excitation and emission of the polymers are in the near visible wavelength region (>390 nm), thus allowing the use of solid state instrumentation and potentially minimize interferences that generally occur in the UV wavelength region.

In at least one embodiment the fluorescent monomer is selected from the group consisting of a compound of: Formula I, Formula II, and any combination thereof.

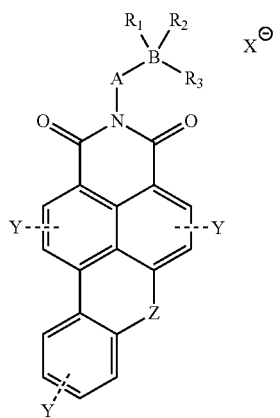

Formula I

-continued

Formula II

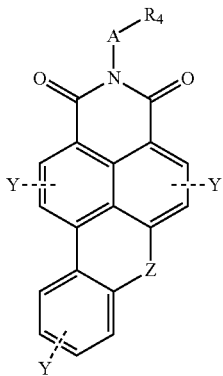

In Formula I: Y is one or more of the following: H, F, Cl, Br, $NO_2$, $CO_2H$ and its salts, $PO_3H_2$ and it salts, $SO_3H$ and its salts, $SO_2NH_2$ or $SO_2NR_2$; Z is one of the following: $CH_2$, C=O, $CR_2$, NH, NR, $NH_2^+$, $NR_2^+$, NOH, O, S, SO, or $SO_2$; $R_1$ and $R_2$ are alkyl; $R_3$ is selected from the group consisting of allyl, 2-hydroxy-3-allyloxy-propyl, vinyl benzyl, 3-methacrylamidopropyl, 3-acrylamidopropyl, 2-acryloxyethyl and 2-methacryloxyethyl. A is selected from the group consisting of alkyl, alkyloxyalkyl, alkylamidoalkyl, aryl or nonexistent; with the proviso that when A is nonexistent, B is nitrogen (N) and B is bonded directly to the imide nitrogen. B is sulfur or nitrogen with the proviso that when B is sulfur only one of $R_1$ or $R_2$ is present; X is an anionic counter ion;

In Formula II: Y is one or more of the following: H, F, Cl, Br, $NO_2$, $CO_2H$ and its salts, $PO_3H_2$ and it salts, $SO_3H$ and its salts, $SO_2NH_2$ or $SO_2NR_2$; Z is one of the following: $CH_2$, C=O, $CR_2$, NH, NR, $NH_2^+$, $NR_2^+$, NOH, O, S, SO, or $SO_2$; A is selected from the group consisting of alkyl, alkyloxyalkyl, alkoxy, alkylamidoalkyl, alkylamino, NH, aryl or nonexistent; $R_4$ is selected from the group consisting of allyl, acryl, methacryl, 2-hydroxy-3-allyloxy-propyl, vinyl benzyl, 2-acryloxyethyl and 2-methacryloxyethyl.

In at least one embodiment, Y is sulfonic acid or hydrogen; Z is O or $SO_2$; $R_1$ and $R_2$ are alkyl; $R_3$ is 2-hydroxy-3-allyloxy-propyl, allyl, vinyl benzyl, or 3-methacrylamidopropyl; B is nitrogen; A is an alkyl group of 1 to 10 carbon atoms; and X is an anionic counter ion.

Acceptable names for Formula I monomeric units are:
Sulfonated-N-(3-N',N'-Dimethylaminopropyl) Benzo (k,l) xanthene-3,4-dicarboxylic imide, 2-Hydroxy-3-Allyloxypropyl Quat and Sulfonated-N-(3-N',N'-Dimethylaminopropyl) Benzo (k,l) sulfonylxanthene-3,4-dicarboxylic imide, 2-Hydroxy-3-Allyloxypropyl Quat.

Monomers of Formula I can be synthesized by reacting a benzoxanthene dicarboxylic anhydride or a sulfonated benzoxanthene dicarboxylic anhydride with a primary amine. The amine can be aliphatic, vinyl, substituted aliphatic or hydrazine. Suitable solvents include water, glacial acetic acid or any solvent system suitable for forming the aromatic fluorescent core. Materials required for these syntheses are commercially available and can be obtained from Aldrich. Polymerizable moieties can be introduced through substitution on the aromatic ring or during quaterization or imidization.

"Tagging" the polymer through the use of the fluorescent monomers of this invention is achieved by synthesizing the polymer in the presence of the fluorescent monomer.

In at least one embodiment, Formula I and, or Formula II is used to synthesize tagged treatment polymers of formulas:
(1) $G_a Q_j W_t$ and (2) $G_a Q_v W_f S_c$, wherein:

For $G_a Q_j W_t$: (1)

G is selected from the group consisting of Formula I and/or Formula II, as previously defined; Q is selected from the group consisting of acrylic acid and salts thereof, methacrylic acid and salts thereof, maleic acid and salts thereof, maleic anhydride, acrylamide, crotonic acid, acrylamidomethylpropane sulfonic acid and salts thereof;

W is selected from the group consisting of:
acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, diallylamine, acid salts of diallylamine, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, and N-vinylpyrrolidone;
with the proviso that Q and W cannot both be the same;
a is from about 0.001 to about 10.0 mole percent;
j is from about 0 to about 99.999 mole percent;
t is from about 0 to about 99.999 mole percent; and
a+j+t=100.

For $G_a Q_v W_f S_c$: (2)

G is as previously defined; Q is as previously defined; W is as previously defined, with the proviso that Q and W cannot both be the same;
S is selected from the group consisting of sulfomethylacrylamide and sulfoethylacrylamide;
a is from about 0.001 to about 10.00 mole percent;
v is from about 0 to about 97.999 mole percent;
f is from about 1 to about 97.999 mole percent;
c is from about 1 to about 40 mole percent; and
a+v+f+c=100.

These tagged treatment polymers can be synthesized by following the procedure for conventional free radical polymerization in an aqueous medium. They can be made by water-in-oil polymerization methods or dispersion polymerization methods or solution polymerization methods. For those tagged treatment polymers containing a sulfomethylated or sulfoethylated acrylamide, the polymers are first created with an acrylamide moiety, and then the acrylamide groups are sulfomethylated using a suitable "sulfo" reagent such as formaldehyde and sodium metabisulfite.

Procedure for Synthesizing Water-In-Oil Emulsion Polymers

The preparation of high molecular weight water-in-oil emulsion polymers has been described in the following references: U.S. Pat. No. 2,982,749 assigned to The Dow Chemical Company; U.S. Pat. No. 3,284,393 assigned to The Dow Chemical Company; U.S. Pat. No. 3,734,873 assigned to Nalco Chemical Company; "Mechanism, Kinetics and Modeling of the Inverse-Microsuspension Homopolymerization of Acrylamide," by Hundeler, D., Hamielec, A. and Baade, W., Polymer (1989), 30(1), 127-42; and "Mechanism, Kinetics and Modeling of Inverse-Microsuspension Polymerization: 2. Copolymerization of Acrylamide with Quaternary Ammonium Cationic Monomers," by D. Hunkeler and A. E. Hamielec; Polymer (1991), 32(14), 2626-40.

A general procedure for the manufacture of water-in-oil emulsion tagged treatment polymers is provided to illustrate the preparation of these tagged treatment polymers using fluorescent monomers. The types and quantities of specific components in the formula (monomers, initiators, Chain Transfer Agents, for example) will vary depending upon the type of polymer (cationic, anionic, nonionic) that is being synthesized.

An aqueous phase is prepared by mixing together in water one or more water soluble monomers, and different polymerization additives such as inorganic salts, chelants, pH buffers, Chain Transfer Agents and Branching or Cross-Linking Agents. In order to synthesize the tagged treatment polymers of the instant claimed invention, a monomer of formula Formula I and, or Formula II is included in the aqueous phase at the desired level.

An organic phase is prepared by mixing together an inert hydrocarbon liquid with one or more oil soluble surfactants. The surfactant mixture should have a low HLB, to ensure the formation of an oil continuous emulsion. Appropriate surfactants for water-in-oil emulsion polymerizations, which are commercially available, are compiled in the North American Edition of McCutcheon's Emulsifiers & Detergents. The oil phase may need to be heated to ensure the formation of a homogeneous oil solution.

The oil phase is charged into a reactor equipped with a mixer, a thermocouple, a nitrogen purge tube, and a condenser. Adding the aqueous phase to the reactor containing the oil phase with vigorous stirring forms an emulsion. The resulting emulsion is heated to the desired temperature, purged with nitrogen, and a free-radical initiator is added. The reaction mixture is stirred for several hours under a nitrogen atmosphere at the desired temperature. Upon completion of the reaction, the water-in-oil emulsion polymer is cooled to room temperature, where any desired post-polymerization additives, such as antioxidants, or a high HLB surfactant (as described in U.S. Pat. No. 3,734,873) may be added.

The resulting emulsion polymer is a free-flowing liquid. An aqueous solution of the water-in-oil emulsion polymer can be generated by adding a desired amount of the emulsion polymer to water with vigorous mixing in the presence of a high-HLB surfactant (as described in U.S. Pat. No. 3,734,873).

Procedure for Synthesizing Dispersion Polymers

The preparation of dispersion polymers has been described in the following references: U.S. Pat. No. 4,929,655, assigned to Hymo Corporation; U.S. Pat. No. 5,006,590, assigned to Hymo Corporation; U.S. Pat. No. 5,597,859, assigned to Nalco Chemical Company; European Patent 657,478; U.S. Pat. No. 5,597,858, assigned to Nalco Chemical Company and European Patent 630,909.

A general procedure for the manufacture of dispersion tagged treatment polymers is provided in the following text in order to illustrate the preparation of dispersion tagged treatment polymers comprising the fluorescent monomers described herein. The types and quantities of specific components in the formula (salts and stabilizer polymers, for example) will vary depending upon the type of polymer (cationic, anionic, nonionic) that is being synthesized.

An aqueous solution containing one or more inorganic salts, one or more water-soluble monomers, any polymerization additives such as chelants, pH buffers, Chain Transfer Agents, Branching or Cross-Linking Agents and a water-soluble stabilizer polymer is charged to a reactor equipped with a mixer, a thermocouple, a nitrogen purging tube, and a water condenser. The monomer solution is mixed vigorously, heated to the desired temperature, and then a water-soluble initiator is added. The solution is purged with nitrogen while maintaining temperature and mixing for several hours. After this time, the products are cooled to room temperature, and any post-polymerization additives are charged to the reactor. Water continuous dispersions of water-soluble polymers are free flowing liquids with product viscosities generally 100-10,000 cP, measured at low shear. Thus, in order to prepare tagged polymers as dispersions, a monomer of formula Formula I and, or Formula II is included in the reaction mixture at the desired level.

Procedure for Synthesizing Solution Polymers

A general procedure for the manufacture of solution polymers is provided to illustrate the preparation of the solution tagged treatment polymers comprising the fluorescent monomers described herein. One typical process is described as follows: One or more monomers are added to a vessel followed by neutralization with a suitable base. The fluorescent monomer can then be added to this monomer solution after neutralization or alternatively, to the reaction vessel. A determined amount of water is then added to the reaction vessel, which is then heated and purged. Polymerization catalysts may also be added to the vessel initially or fed in gradually during the course of the reaction. Water soluble polymerization initiators such as any azo or redox initiator or combination thereof are added along with the monomer solution to the reaction mixture in separate feeds over the same amount of time, usually 2 to 6 hours. The reaction temperature is maintained at about 60-70° C. Additional initiator may be used after addition is complete to reduce residual monomer levels.

The amount of fluorescent monomer that is used should be an amount sufficient to allow the tagged treatment polymer to be detected in the aqueous environment that it is used. The minimum amount of fluorescent moiety that can be used is that amount which gives a signal-to-noise ratio (S/N) of 3 at the desired tagged treatment polymer dosage. The signal-to-noise ratio is that value where the magnitude of the transduced signal (including but not limited to electronic and optical signals) due to the presence of a target analytic in a measurement device is greater than or equal to a level three (3) times the magnitude of a transduced signal where the analyte (species) of interest is not present in the measurement device.

The amount of fluorescent monomer in the tagged treatment polymers is in the range of from about 0.001 mole percent to about 10 mole percent, preferably from about 0.01 mole percent to about 0.4 mole percent, and most preferably from about 0.05 mole percent to about 0.35 mole percent. For purposes of this patent application, mole percent of all monomers in the tagged treatment polymer is calculated based on weight percent. For purposes of this patent application, the subscripts a, j, t, v, f and c refer to the mole percent of each monomer component of the tagged treatment polymers.

The remainder of the tagged treatment polymer can have one, two or three additional monomers in it.

All molecular weights in this patent application are weight average molecular weights measured by gel permeation chromatography (GPC) calculated from both refractive index and fluorescent detector traces using polystyrene sulfonate (PSS) molecular weight standards. Tagged treatment polymers that have a wide range of molecular weights can be prepared by using the procedures described previously by those skilled in the art.

The molecular weights of the instant claimed tagged treatment polymers are from about 500 atomic mass units (hereinafter "a.m.u.") to about 10,000,000 a.m.u. Preferably the molecular weights are from about 2000 a.m.u. to about 500,000 a.m.u. Most preferably, the molecular weights are from about 5000 a.m.u. to about 40,000 a.m.u.

Preferred tagged polymers are made via solution polymerization techniques and have a molecular weight from about 5,000 a.m.u. to about 40,000 a.m.u.

Preferred tagged treatment polymers are where said fluorescent monomer is selected from the group consisting of:

Sulfonated-N-(3-N',N'-Dimethylaminopropyl) Benzo (k,l) xanthene-3,4-dicarboxylic imide, 2-Hydroxy-3-Allyloxypropyl Quat (S-NDMAPBXA-DCI-HAPQ)

The more preferred polymers are where G is Formula I as previously defined; Q, if present in the polymer, is selected from the group consisting of acrylamide and acrylic acid; W, if present in the polymer, is selected from the group consisting of acrylamide and acrylamidomethylpropane sulfonic acid; and S, if present in the polymer, is N-sulfomethylacrylamide.

The most preferred polymers are selected from the group consisting of 0.2 mole % S-NDMAPBXA-DCI-HAPQ/80.9 mole % Acrylic Acid/ 18.9 mole % Acrylamidomethylpropane sulfonic acid.

Once created the tagged treatment polymers of the instant claimed invention can be used as scale inhibitors in industrial water systems. As these polymers are consumed performing that function, their fluorescent signal will decrease and thus the decrease in the fluorescent signal can be used to indicate that undesired scaling is taking place.

The tagged treatment polymers containing a fluorescent monomer can be used in industrial water systems. Examples of industrial water systems are cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, paper production, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

The tagged treatment polymer comprising a fluorescent monomer may be used in the industrial water systems singly or in combination with other polymers, which are not tagged. The dosage rate of tagged treatment polymer in an industrial water system, when it is being used as a scale inhibitor, is from about 1 to about 100 milligrams of solid component active per liter of water.

At least one embodiment of the invention is a process for the inhibition of scale formation in an industrial water system which comprises introducing into said industrial water system a tagged treatment polymer, previously described, in an amount sufficient to inhibit scale formation. The amount of the tagged treatment polymer comprising the fluorescent monomer added to an industrial water system is in the range of about 1.0 milligrams (mg) to about 30 milligrams of the total solid polymer actives per liter of water in the system. This is equivalent to about 1 part per million (ppm) to about 30 ppm.

When used in an industrial water system, the fluorescent signal of the tagged treatment polymers can be used to determine how much tagged treatment polymer is present in the industrial water system. A least one embodiment of the invention is:

A method for maintaining the desired amount of tagged treatment polymer in an industrial water system comprising the steps of:

i) adding to said industrial water system a tagged treatment polymer, wherein said tagged treatment polymer is as previously described;

ii) using a fluorometer to detect the fluorescent signal of said tagged treatment polymer;

iii) converting the fluorescent signal of said tagged treatment polymer to the concentration of said tagged treatment polymer; and iv) adjusting the concentration of said tagged treatment polymer according to what the desired concentration is for said tagged treatment polymer in said industrial water system.

At least one embodiment of the invention is a method for maintaining the desired amount of tagged treatment polymer in an industrial water system comprising the steps of:

a) adding an inert tracer and a tagged treatment polymer, as previously described, to water such that a desired concentration of said tagged treatment polymer is present in said water;

b) using a fluorometer to detect the fluorescent signals of said inert tracer and said tagged treatment polymer;

c) converting the fluorescent signals of said inert tracer and said tagged treatment polymer to the concentration of said inert tracer and said tagged treatment polymer; and d) adjusting the concentration of said tagged treatment polymer according to what the desired concentration is for said tagged treatment polymer in the industrial water system.

Additional Embodiments

1. A fluorescent monomer selected from the group consisting of compounds of the formula:

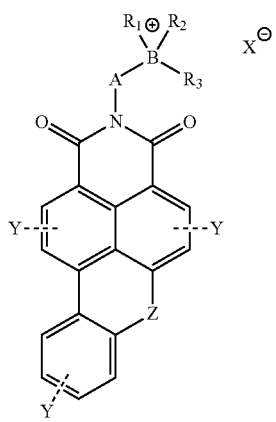

(Formula I)

wherein Y is one or more of the following: H, F, Cl, Br, NO$_2$, CO$_2$H and its salts, PO$_3$H$_2$ and it salts, SO$_3$H and its salts, SO$_2$NH$_2$ or SO$_2$NR$_2$;

Z is one of the following: CH$_2$, C=O, CR$_2$, NH, NR, NH$_2^+$, NR$_2^+$, NOH, O, S, SO, or SO$_2$, R$_1$ and R$_2$ are alkyl R$_3$ is selected from the group consisting of allyl, 2-hydroxy-3-allyloxy-propyl, vinyl benzyl, 3-methacrylamidopropyl, 3-acrylamidopropyl, 2-acryloxyethyl and 2-methacryloxyethyl.

A is selected from the group consisting of alkyl, alkyloxyalkyl, alkylamidoalkyl, aryl or nonexistent; with the proviso that when A is nonexistent, B is nitrogen (N) and B is bonded directly to the imide nitrogen.

B is sulfur or nitrogen with the proviso that when B is sulfur only one of R$_1$ or R$_2$ is present;

X is an anionic counter ion;

2. A fluorescent monomer of claim 1, wherein said monomer is sulfonated-N-(3-N', N'-Dimethylaminopropyl) benzo (k,l) xanthene-3,4-dicarboxylic imide, 2-hydroxy-3-allyloxypropyl quaternary salt.

3. A fluorescent monomer of claim 1, wherein said monomer is sulfonated —N-(3-N', N'-Dimethylaminopropyl) benzo (k,l) xanthene-3,4-dicarboxylic imide, vinyl benzyl chloride quaternary salt.

4. A fluorescent monomer of claim 1, wherein said monomer is sulfonated —N-(3-N', N'-Dimethylaminopropyl) benzo (k,l) xanthene-3,4-dicarboxylic imide, allyl chloride quaternary salt.

5. A tagged treatment polymer selected from the group consisting of:

$$G_a Q_j W_t \quad (1)$$

wherein G is selected from the group consisting of:

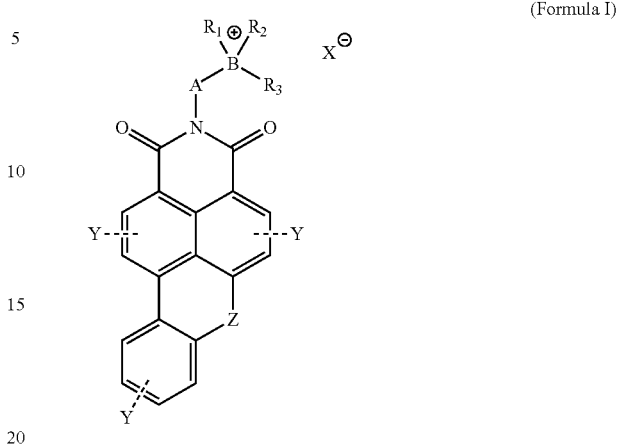

(Formula I)

wherein Y is one or more of the following: H, F, Cl, Br, NO$_2$, CO$_2$H and its salts, PO$_3$H$_2$ and it salts, SO$_3$H and its salts, SO$_2$NH$_2$ or SO$_2$NR$_2$;

Z is one of the following: CH$_2$, C=O, CR$_2$, NH, NR, NH$_2^+$, NR$_2^+$, NOH, O, S, SO, or SO$_2$;

R$_1$ and R$_2$ are alkyl

R$_3$ is selected from the group consisting of allyl, 2-hydroxy-3-allyloxy-propyl, vinyl benzyl, 3-methacrylamidopropyl, 3-acrylamidopropyl, 2-acryloxyethyl and 2-methacryloxyethyl.

A is selected from the group consisting of alkyl, alkyloxyalkyl, alkylamidoalkyl, aryl or nonexistent; with the proviso that when A is nonexistent, B is nitrogen (N) and B is bonded directly to the imide nitrogen.

B is sulfur or nitrogen with the proviso that when B is sulfur only one of R$_1$ or R$_2$ is present;

X is an anionic counter ion;

wherein Q is selected from the group consisting of acrylic acid and salts thereof, methacrylic acid and salts thereof, maleic acid and salts thereof, maleic anhydride, acrylamide, crotonic acid, acrylamidomethylpropane sulfonic acid and salts thereof;

wherein W is selected from the group consisting of: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, diallylamine, acid salts of diallylamine, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, and N-vinylpyrrolidone;
with the proviso that Q and W cannot both be the same:
wherein a is from about 0.001 to about 10.0 mole percent;
wherein j is from about 0 to about 99.999 mole percent;
wherein t is from about 0 to about 99.999 mole percent; and
wherein a+j+t=100;

$$G_a Q_v W_f S_c \qquad (2)$$

wherein G is as previously defined;
wherein Q is as previously defined;
wherein W is as previously defined, with the proviso that Q and W cannot both be the same;
wherein S is selected from the group consisting of sulfomethylacrylamide and sulfoethylacrylamide;
wherein a is from about 0.001 to about 10.00 mole percent;
wherein v is from about 0 to about 97.999 mole percent;
wherein f is from about 1 to about 97.999 mole percent;
wherein c is from about 1 to about 40 mole percent; and
wherein a+v+f+c=100.

6. A tagged treatment polymer of claim 5 wherein G is sulfonated-N-(3-N',N'-Dimethylaminopropyl)benzo (k,l) xanthene-3,4-dicarboxylic imide, 2-hydroxy-3-allyloxypropyl quaternary salt 7. A tagged treatment polymer of claim 5 wherein G is sulfonated-N-(3-N',N'-Dimethylaminopropyl) benzo (k,l) xanthene-3,4-dicarboxylic imide, vinyl benzyl chloride quaternary salt.

8. A tagged treatment polymer of claim 5 wherein G is sulfonated-N-(3-N',N'-Dimethylaminopropyl) benzo (k,l) xanthene-3,4-dicarboxylic imide, allyl chloride quaternary salt.

9. A tagged treatment polymer of claim 5 wherein Q is acrylic acid and W is acrylamide.

10. A tagged treatment polymer of claim 5 wherein Q is acrylamide, W is acrylic acid and S is N-sulfomethylacrylamide.

11. A tagged treatment polymer of claim 5 wherein Q is acrylic acid and W is acrylamidomethylpropane sulfonic acid.

12. A tagged treatment polymer of claim 5 wherein G is sulfonated-N-(3-N',N'-Dimethylaminopropyl) benzo (k,l) xanthene-3,4-dicarboxylic imide, 2-hydroxy-3-allyloxypropyl quaternary salt, Q is acrylic acid, W is acrylamide and S is N sulfomethylacrylamide.

13. A tagged treatment polymer of claim 5 wherein G is sulfonated-N-(3-N',N'-Dimethylaminopropyl) benzo (k,l) xanthene-3,4-dicarboxylic imide, vinyl benzyl chloride quaternary salt, Q is acrylic acid, W is acrylamide and S is N sulfomethylacrylamide.

14. A tagged treatment polymer of claim 5 wherein G is sulfonated-N-(3-N',N'-Dimethylaminopropyl) benzo (k,l) xanthene-3,4-dicarboxylic imide, allyl chloride quaternary salt, Q is acrylic acid, W is acrylamide and S is N sulfomethylacrylamide.

15. A tagged treatment polymer of claim 5 wherein G is sulfonated-N-(3-N',N'-Dimethylaminopropyl) benzo (k,l) xanthene-3,4-dicarboxylic imide, 2-hydroxy-3-allyloxypropyl quaternary salt, Q is acrylic acid, W is acrylamidomethylpropane sulfonic acid.

16. A tagged treatment polymer of claim 5 wherein G is sulfonated-N-(3-N',N'-Dimethylaminopropyl) benzo ((k,l) xanthene-3,4-dicarboxylic imide, vinyl benzyl chloride quaternary salt, Q is acrylic acid, W is acrylamidomethylpropane sulfonic acid.

17. A tagged treatment polymer of claim 5 wherein G is sulfonated-N-(3-N',N'-Dimethylaminopropyl) benzo ((k,l) xanthene-3,4-dicarboxylic imide, allyl chloride quaternary salt, Q is acrylic acid, W is acrylamidomethylpropane sulfonic acid.

18. A tagged treatment polymer of claim 5 wherein G is sulfonated —N-(3-N',N'-Dimethylaminopropyl) benzo ((k,l) xanthene-3,4-dicarboxylic imide, 2-hydroxy-3-allyloxypropyl quaternary salt and Q is acrylic acid.

19. A process for the inhibition of scale formation in an industrial water system which comprises introducing into said industrial water system a tagged treatment polymer selected from the group consisting of:

$$G_a Q_j W_t \qquad (1)$$

wherein G is selected from the group consisting of:

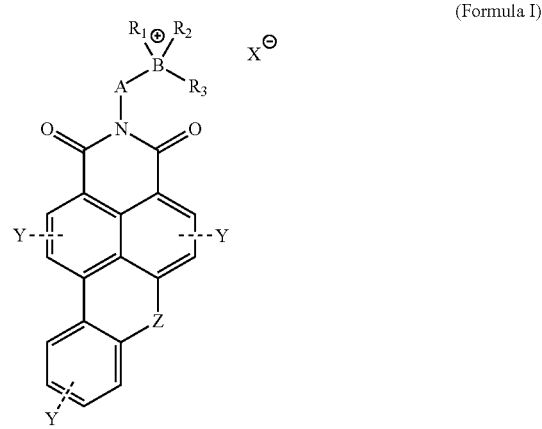

(Formula I)

wherein Y is one or more of the following: H, F, Cl, Br, $NO_2$, $CO_2H$ and its salts, $PO_3H_2$ and it salts, $SO_3H$ and its salts, $SO_2NH_2$ or $SO_2NR_2$;

Z is one of the following: $CH_2$, C=O, $CR_2$,NH, NR, $NH_2^+$, $NR_2^+$, NOH, O, S, SO, or $SO_2$;

$R_1$ and $R_2$ are alkyl $R_3$ is selected from the group consisting of allyl, 2-hydroxy-3-allyloxy-propyl, vinyl benzyl, 3-methacrylamidopropyl, 3-acrylamidopropyl, 2-acryloxyethyl and 2-methacryloxyethyl.

A is selected from the group consisting of alkyl, alkyloxyalkyl, alkylamidoalkyl, aryl or nonexistent; with the proviso that when A is nonexistent, B is nitrogen (N) and B is bonded directly to the imide nitrogen.

B is sulfur or nitrogen with the proviso that when B is sulfur only one of $R_1$ or $R_2$ is present;

X is an anionic counter ion;
wherein Q is selected from the group consisting of acrylic acid and salts thereof, methacrylic acid and salts thereof, maleic acid and salts thereof, maleic anhydride, acrylamide, crotonic acid, acrylamidomethylpropane sulfonic acid and salts thereof;
wherein W is selected from the group consisting of: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, diallylamine, acid salts of diallylamine, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, and N-vinylpyrrolidone;

with the proviso that Q and W cannot both be the same;
wherein a is from about 0.001 to about 10.0 mole percent;
wherein j is from about 0 to about 99.999 mole percent;
wherein t is from about 0 to about 99.999 mole percent; and
wherein a+j+t=100;

$$G_a Q_v W_f S_c \quad (2)$$

wherein G is as previously defined;
wherein Q is as previously defined;
wherein W is as previously defined, with the proviso that Q and W cannot both be the same;
wherein S is selected from the group consisting of sulfomethylacrylamide and sulfoethylacrylamide;
wherein a is from about 0.001 to about 10.00 mole percent;
wherein v is from about 0 to about 97.999 mole percent;
wherein f is from about 1 to about 97.999 mole percent;
wherein c is from about 1 to about 40 mole percent; and
wherein a+v+f+c=100;
in an amount sufficient to inhibit scale formation.

20. A tagged treatment polymer of claim 19 wherein Q is acrylic acid and W is acrylamide.
21. A tagged treatment polymer of claim 19 wherein Q is acrylamide, W is acrylic acid and S is N-sulfomethylacrylamide.
22. A tagged treatment polymer of claim 19 wherein Q is acrylic acid and W is acrylamidomethylpropane sulfonic acid.
23. A tagged treatment polymer of claim 19 wherein G is sulfonated-N-(3-N',N'-Dimethylaminopropyl) benzo ((k,l) xanthene-3,4-dicarboxylic imide, 2-hydroxy-3-allyloxypropyl quaternary salt, Q is acrylic acid, W is acrylamide and S is N sulfomethylacrylamide.
24. A tagged treatment polymer of claim 19 wherein G is sulfonated-N-(3-N',N'-Dimethylaminopropyl)benzo ((k,l) xanthene-3,4-dicarboxylic imide, vinyl benzyl chloride quaternary salt, Q is acrylic acid, W is acrylamide and S is N sulfomethylacrylamide.
25. A tagged treatment polymer of claim 19 wherein G is sulfonated-N-(3-N',N'-Dimethylaminopropyl) benzo ((k,l) xanthene-3,4-dicarboxylic imide, allyl chloride quaternary salt, Q is acrylic acid, W is acrylamide and S is N sulfomethylacrylamide.
26. A tagged treatment polymer of claim 19 wherein G is sulfonated-N-(3-N',N'-Dimethylaminopropyl) benzo ((k,l) xanthene-3,4-dicarboxylic imide, 2-hydroxy-3-allyloxypropyl quaternary salt, Q is acrylic acid, W is acrylamidomethylpropane sulfonic acid.
27. A tagged treatment polymer of claim 19 wherein G is sulfonated-N-(3-N',N'-Dimethylaminopropyl) benzo ((k,l) xanthene-3,4-dicarboxylic imide, vinyl benzyl chloride quaternary salt, Q is acrylic acid, W is acrylamidomethylpropane sulfonic acid.
28. A tagged treatment polymer of claim 19 wherein G is sulfonated-N-(3-N',N'-Dimethylaminopropyl) benzo ((k,l) xanthene-3,4-dicarboxylic imide, allyl chloride quaternary salt, Q is acrylic acid, W is acrylamidomethylpropane sulfonic acid.
29. A tagged treatment polymer of claim 19 wherein G is sulfonated-N-(3-N',N'-Dimethylaminopropyl) benzo ((k,l) xanthene-3,4-dicarboxylic imide, 2-hydroxy-3-allyloxypropyl quaternary salt and Q is acrylic acid.
30. A method for maintaining the desired amount of tagged treatment polymer in an industrial water system comprising the steps of:
i) adding to said industrial water system a tagged treatment polymer, selected from a group consisting of:

$$G_a Q_j W_t \quad (1)$$

wherein G is selected from the group consisting of:

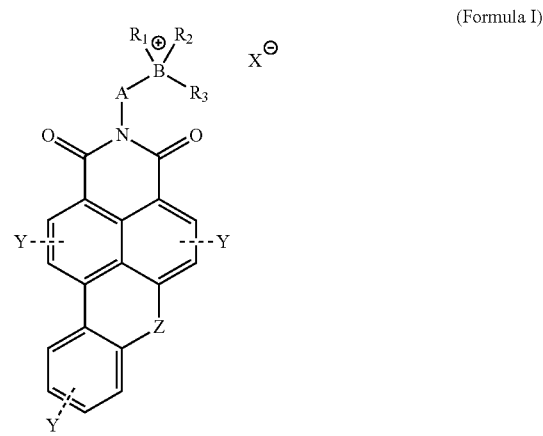

(Formula I)

wherein Y is one or more of the following: H, F, Cl, Br, $NO_2$, $CO_2H$ and its salts, $PO_3H_2$ and it salts, $SO_3H$ and its salts, $SO_2NH_2$ or $SO_2NR_2$;
Z is one of the following: $CH_2$, C=O, $CR_2$, NH, NR, $NH_2^+$, $NR_2^+$, NOH, O, S, SO, or $SO_2$;
$R_1$ and $R_2$ are alkyl
$R_3$ is selected from the group consisting of allyl, 2-hydroxy-3-allyloxy-propyl, vinyl benzyl, 3-methacrylamidopropyl, 3-acrylamidopropyl, 2-acryloxyethyl and 2-methacryloxyethyl.
A is selected from the group consisting of alkyl, alkyloxyalkyl, alkylamidoalkyl, aryl or nonexistent; with the proviso that when A is nonexistent, B is nitrogen (N) and B is bonded directly to the imide nitrogen.

B is sulfur or nitrogen with the proviso that when B is sulfur only one of $R_1$ or $R_2$ is present;

X is an anionic counter ion;

wherein Q is selected from the group consisting of acrylic acid and salts thereof, methacrylic acid and salts thereof, maleic acid and salts thereof, maleic anhydride, acrylamide, crotonic acid, acrylamidomethylpropane sulfonic acid and salts thereof;

wherein W is selected from the group consisting of: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, diallylamine, acid salts of diallylamine, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethacrylate, polyethylene glycol dimethacrylate, glycidyl methacrylate, acrylamidomethylpropane sulfonic acid and the sodium salt thereof, vinyl alcohol, vinyl acetate, and N-vinylpyrrolidone;

with the proviso that Q and W cannot both be the same;

wherein a is from about 0.001 to about 10.0 mole percent;

wherein j is from about 0 to about 99.999 mole percent;

wherein t is from about 0 to about 99.999 mole percent; and wherein $a+j+t=100$;

$$G_a Q_v W_f S_c \qquad (2)$$

wherein G is as previously defined;

wherein Q is as previously defined;

wherein W is as previously defined, with the proviso that Q and W cannot both be the same;

wherein S is selected from the group consisting of sulfomethylacrylamide and sulfoethylacrylamide;

wherein a is from about 0.001 to about 10.00 mole percent;

wherein v is from about 0 to about 97.999 mole percent;

wherein f is from about 1 to about 97.999 mole percent;

wherein c is from about 1 to about 40 mole percent; and wherein $a+v+f+c=100$;

ii) using a fluorometer to detect the fluorescent signal of said tagged treatment polymer;

iii) converting the fluorescent signal of said tagged treatment polymer to the concentration of said tagged treatment polymer; and iv) adjusting the concentration of said tagged treatment polymer according to what the desired concentration is for said tagged treatment polymer in said industrial water system.

31. A tagged treatment polymer of claim 30 wherein Q is acrylic acid and W is acrylamide.

32. A tagged treatment polymer of claim 30 wherein Q is acrylamide, W is acrylic acid and S is N-sulfomethylacrylamide.

33. A tagged treatment polymer of claim 30 wherein Q is acrylic acid and W is acrylamidomethylpropane sulfonic acid.

34. A tagged treatment polymer of claim 30 wherein G is sulfonated —N-(3-N',N'-Dimethylaminopropyl) benzo ((k,l) xanthene-3,4-dicarboxylic imide, 2-hydroxy-3-allyloxypropyl quaternary salt, Q is acrylic acid, W is acrylamide and S is N sulfomethylacrylamide.

35. A tagged treatment polymer of claim 30 wherein G is sulfonated —N-(3-N',N'-Dimethylaminopropyl) benzo ((k,l) xanthene-3,4-dicarboxylic imide, vinyl benzyl chloride quaternary salt, Q is acrylic acid, W is acrylamide and S is N sulfomethylacrylamide.

36. A tagged treatment polymer of claim 30 wherein G is sulfonated —N-(3-N',N'-Dimethylaminopropyl) benzo ((k,l) xanthene-3,4-dicarboxylic imide, allyl chloride quaternary salt, Q is acrylic acid, W is acrylamide and S is N sulfomethylacrylamide.

37. A tagged treatment polymer of claim 30 wherein G is sulfonated —N-(3-N',N'-Dimethylaminopropyl) benzo ((k,l) xanthene-3,4-dicarboxylic imide, 2-hydroxy-3-allyloxypropyl quaternary salt, Q is acrylic acid, W is acrylamidomethylpropane sulfonic acid.

38. A tagged treatment polymer of claim 30 wherein G is sulfonated —N-(3-N',N'-Dimethylaminopropyl) benzo ((k,l) xanthene-3,4-dicarboxylic imide, vinyl benzyl chloride quaternary salt, Q is acrylic acid, W is acrylamidomethylpropane sulfonic acid.

39. A tagged treatment polymer of claim 30 wherein G is sulfonated —N-(3-N',N'-Dimethylaminopropyl) benzo ((k,l) xanthene-3,4-dicarboxylic imide, allyl chloride quaternary salt, Q is acrylic acid, W is acrylamidomethylpropane sulfonic acid.

40. A tagged treatment polymer of claim 30 wherein G is sulfonated —N-(3-N',N'-Dimethylaminopropyl) benzo ((k,l) xanthene-3,4-dicarboxylic imide, 2-hydroxy-3-allyloxypropyl quaternary salt and Q is acrylic acid.

41. A method for maintaining the desired amount of tagged treatment polymer in an industrial water system comprising the steps of:

a) adding an inert tracer and a tagged treatment polymer to the water of an industrial water system, wherein said tagged treatment polymer is selected from the group consisting of:

$$G_a Q_j W_t \qquad (1)$$

wherein G is selected from the group consisting of:
wherein G is selected from the group consisting of:

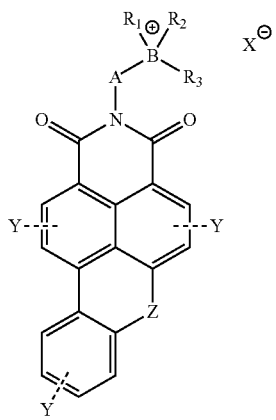

(Formula I)

wherein Y is one or more of the following: H, F, Cl, Br, $NO_2$, $CO_2H$ and its salts, $PO_3H_2$ and it salts, $SO_3H$ and its salts, $SO_2NH_2$ or $SO_2NR_2$;

Z is one of the following: $CH_2$, C=O, $CR_2$, NH, NR, $NH_2^+$, $NR_2^+$, NOH, O, S, SO, or $SO_2$;

$R_1$ and $R_2$ are alkyl $R_3$ is selected from the group consisting of allyl, 2-hydroxy-3-allyloxy-propyl, vinyl benzyl, 3-methacrylamidopropyl, 3-acrylamidopropyl, 2-acryloxyethyl and 2-methacryloxyethyl.

A is selected from the group consisting of alkyl, alkyloxyalkyl, alkylamidoalkyl, aryl or nonexistent; with the proviso that when A is nonexistent, B is nitrogen (N) and B is bonded directly to the imide nitrogen.

B is sulfur or nitrogen with the proviso that when B is sulfur only one of $R_1$ or $R_2$ is present;

X is an anionic counter ion;

wherein Q is selected from the group consisting of acrylic acid and salts thereof, methacrylic acid and salts thereof, maleic acid and salts thereof, maleic anhydride, acrylamide, crotonic acid, acrylamidomethylpropane sulfonic acid and salts thereof;

wherein W is selected from the group consisting of: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, diallyamine, acid salts of diallylamine, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, and N-vinylpyrrolidone;

with the proviso that Q and W cannot both be the same;
wherein a is from about 0.001 to about 10.0 mole percent;
wherein j is from about 0 to about 99.999 mole percent;
wherein t is from about 0 to about 99.999 mole percent; and
wherein a+j+t=100;

$$G_a Q_v W_f S_c \quad (2)$$

wherein G is as previously defined;
wherein Q is as previously defined;
wherein W is as previously defined, with the proviso that Q and W cannot both be the same;
wherein S is selected from the group consisting of sulfomethylacrylamide and sulfoethylacrylamide;
wherein a is from about 0.001 to about 10.00 mole percent;
wherein v is from about 0 to about 97.999 mole percent;
wherein f is from about 1 to about 97.999 mole percent;
wherein c is from about 1 to about 40 mole percent; and
wherein a+v+f+c=100;

such that a desired concentration of said tagged treatment polymer is present in said water;

b) using a fluorometer to detect the fluorescent signals of said inert tracer and said tagged treatment polymer;

c) converting the fluorescent signals of said inert tracer and said tagged treatment polymer to the concentration of said inert tracer and said tagged treatment polymer; and d) adjusting the concentration of said tagged treatment polymer according to what the desired concentration is for said tagged treatment polymer in said industrial water system.

42. A tagged treatment polymer of claim 41 wherein Q is acrylic acid and W is acrylamide.

43. A tagged treatment polymer of claim 41 wherein Q is acrylamide, W is acrylic acid and S is N-sulfomethylacrylamide.

44. A tagged treatment polymer of claim 41 wherein Q is acrylic acid and W is acrylamidomethylpropane sulfonic acid.

45. A tagged treatment polymer of claim 41 wherein G is sulfonated —N-(3-N',N'-Dimethylaminopropyl) benzo ((k,l) xanthene-3,4-dicarboxylic imide, 2-hydroxy-3-allyloxypropyl quaternary salt, Q is acrylic acid, W is acrylamide and S is N sulfomethylacrylamide.

46. A tagged treatment polymer of claim 41 wherein G is sulfonated —N-(3-N',N'-Dimethylaminopropyl) benzo ((k,l) xanthene-3,4-dicarboxylic imide, vinyl benzyl chloride quaternary salt, Q is acrylic acid, W is acrylamide and S is N sulfomethylacrylamide.

47. A tagged treatment polymer of claim 41 wherein G is sulfonated —N-(3-N',N'-Dimethylaminopropyl) benzo ((k,l) xanthene-3,4-dicarboxylic imide, allyl chloride quaternary salt, Q is acrylic acid, W is acrylamide and S is N sulfomethylacrylamide.

48. A tagged treatment polymer of claim 41 wherein G is sulfonated —N-(3-N',N'-Dimethylaminopropyl) benzo ((k,l) xanthene-3,4-dicarboxylic imide, 2-hydroxy-3-allyloxypropyl quaternary salt, Q is acrylic acid, W is acrylamidomethylpropane sulfonic acid.

49. A tagged treatment polymer of claim 41 wherein G is sulfonated —N-(3-N',N'-Dimethylaminopropyl) benzo ((k,l) xanthene-3,4-dicarboxylic imide, vinyl benzyl chloride quaternary salt, Q is acrylic acid, W is acrylamidomethylpropane sulfonic acid.

50. A tagged treatment polymer of claim 41 wherein G is sulfonated —N-(3-N',N'-Dimethylaminopropyl) benzo (k,l) xanthene-3,4-dicarboxylic imide, allyl chloride quaternary salt, Q is acrylic acid, W is acrylamidomethylpropane sulfonic acid.

51. A tagged treatment polymer of claim 41 wherein G is sulfonated —N-(3-N',N'-Dimethylaminopropyl) benzo ((k,l) xanthene-3,4-dicarboxylic imide, 2-hydroxy-3-allyloxypropyl quaternary salt and Q is acrylic acid.

52. A tagged treatment polymer of claim 41 wherein G is sulfonated —N-(3-N',N'-Dimethylaminopropyl) benzo ((k,l) xanthene-3,4-dicarboxylic imide, vinylbenzyl chloride quaternary salt and Q is acrylic acid.

EXAMPLES

The foregoing may be better understood by reference to the following examples, which is presented for purposes of illustration and is not intended to limit the scope of the invention.

Monomer Example 1

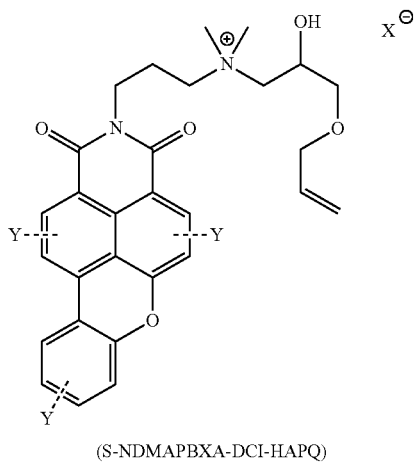

(S-NDMAPBXA-DCI-HAPQ)

Preparation of Sulfonated —N-(3-N',N'-Dimethylaminopropyl) Benzo (k,l) xanthene-3,4-dicarboxylic imide, 2-Hydroxy-3-Allyloxypropyl Quat (S-NDMAPBXA-DCI-HAPQ) Benzoxanthene was synthesized according to the method of A. T. Peters and Y. S. S. Behesti in The Journal of the Society of Dyers and Colorists, 1989, 105, pages 29 to 35 and sulfonated according to the procedure described by H. Troster U.S. Pat. No. 3,888,863.

Step One:
Synthesis of Sulfonated —N-(3-N',N'-Dimethylaminopropyl) Benzo (k,l) xanthene-3,4-dicarboxylic imide (I)

A 25 ml round bottom flask was charged with sulfonated benzo (k,l) xanthene-3,4-dicarboxylic imide (0.5 g, 0.714 mmol, 64%), 6.5 mL water and 0.15 g glacial acetic acid. 3-(dimethylamino)-1-propyl amine (0.131 g, 1.28 mmol) was added dropwise. The mixture was refluxed for 5 hours and cooled. The solution was concentrated to dryness to give the product.

Step 2:
Sulfonated —N-(3-N',N'-Dimethylaminopropyl) Benzo (k,l) xanthene-3,4-dicarboxylic imide, 2-Hydroxy-3-Allyloxypropyl Quat (S-NDMAPBXA-DCI-HAPQ)

A 100 ml round bottom flask charged with I (2 g, 3.76 mmol) and 37.6 mL of water. Potassium carbonate (1.04 g, 7.52 mmol) and 0.52 g of allyl glycidyl ether were added and the mix was heated to 50° C. for 2.5 hours to form the product.

Polymer Example 1

Preparation of 0.2 mole % S-NDMAPBXA-DCI-HAPQ/ 80.9 mole % Acrylic Acid/18.9 mole % Acrylamidomethylpropane sulfonic acid A reactor was charged with deionized water (93.6 g) and S-NDMAPBXA-DCI-HAPQ (prepared according to Monomer Example 1, 30.2 g, 5.8 mmol) was heated to 65°C with stirring (750 rpm). At temperature, initiator solution 1 (2.3 g sodium persulfate in 6.8 g of deionized water), and initiator solution 2 (7.7 g sodium metabisulfite in 12.5 g of deionized water) were added separately at a constant flow rate over a period of 3.25 hours. Five minutes after initiator feed had started, a monomer solution 1 (8.2 g deionized water and 135.0 g, 1.875 mol of acrylic acid), and monomer solution 2 (199.1 g, 0.51 mol of 58% Acrylamidomethylpropane sulfonic acid), were added separately at a constant flow rate over a period of 3 hours. After 30 minutes, 50% sodium hydroxide (4.6 g, 0.058 mol) was added. After monomer and initiator feeding was complete, the reaction was held at temperature for an additional 30 minutes.

Method of Use Example 1

Stability and Performance Testing:

The fluorescence properties (excitation and emission maxima) of polymers prepared using the monomers are given in Table I. Excitation maxima are all greater than 390 nm. The fluorescence of the monomers remained invariant over a pH range of approximately 2-12.

Another important feature of these polymers is the stability of the fluorescence in the presence of oxidizing biocides. The oxidizing biocide stability test was performed in the following manner. Solutions of simulated water were prepared with the desired levels of cations and anions at the desired pH. For these experiments the simulated cooling water contained 150 ppm Ca (as $CaCO_3$), 75 ppm Mg (as $CaCO_3$) and 110 ppm alkalinity (as $CaCO_3$). The water was then adjusted to the desired pH with HCl or NaOH. Tests were performed at pH 7 and 8. A series of three amber bottles were labeled with the desired test sample. A 50 ml aliquot of the simulated water was delivered into each of the three labeled bottles. To one of the bottles (labeled "B") was delivered 60 µl of a 1200 ppm stock solution of bleach. To a second bottle (labeled "A") was delivered 60 µl of a 1200 ppm stock solution of Acti-Brom® biocide, available from Nalco an Ecolab Company. To the third bottle (labeled "N") was delivered 60 µl distilled water. The amount of free and total chorine was measured immediately after the samples were prepared and 24 hours later at the time of fluorescence analysis. The bottles were stored for 24 hours in the dark. The levels of free and total chlorine were checked intermittently to ensure that there was a residual. After 24 hours, fluorescence measurements were done using the sample marked "N" as the reference sample. The % fluorescence consumed (hereinafter "% Fl consumed") in the presence of an oxidizing biocide was calculated as shown below. It is important to note that lower levels of % Fl Consumed indicate lower loss of fluorescent emission. Results for the fluorescent monomers are given in Table I.

$$\% F1 \text{ Consumed} = \frac{\text{Intensity of } N \text{ Sample} - \text{Intensity of } B \text{ or } S \text{ Sample}}{\text{Intensity of } N \text{ Sample}} \times 100$$

TABLE I

Summary of Fluorescence Properties and Oxidizing Biocide Stability of a Fluorescent Monomer

| Example | Monomer Name | Fluorescence Properties | Oxidizing Biocide Stability (% Fluorescence Consumed) |
|---|---|---|---|
| 1 | S-NDMAPBXA-DCI-HAPQ | Ex = 426 nm Em = 475 nm | Bleach (pH7) = 2.38% |
| 2 | S-NDMAPBXA-DCI-HAPQ | Ex = 426 nm Em = 475 nm | Acti-Brom® (pH8) = 0.05% |

When using the tagged treatment polymer as a compound of a scale-inhibitor product in an industrial water system, the only decrease or loss of fluorescence signal from the polymer should be due to loss of the polymer under scaling conditions. When identifying a scaling event as the reason for a loss of fluorescence, it is undesirable for the level of fluorescence to also vary based on pH changes, other components present in the cooling water system, or from oxidizing biocides such as the Acti-Brom® biocide system.

If the amount consumed by an oxidizing biocide is equal to or less than 10% of the signal, then the tagged treatment polymer can be used in an industrial water system. Although a small amount of the tagged treatment polymer is consumed in the presence of 2 ppm Acti-Brom® biocide, the results given above indicate that the tagged treatment polymers are sufficiently stable to be used in industrial water systems where Acti-Brom® is present.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and/or incorporated herein. In addition the invention encompasses any possible combination that also specifically excludes any one or more of the various embodiments described herein and/or incorporated herein.

The above disclosure is intended to be illustrative and not exhaustive. This description will suggest many variations and alternatives to one of ordinary skill in this art. The compositions and methods disclosed herein may comprise, consist of, or consist essentially of the listed components, or steps. As used herein the term "comprising" means "including, but not limited to". As used herein the term "consisting essentially of" refers to a composition or method that includes the disclosed components or steps, and any other components or steps that do not materially affect the novel and basic characteristics of the compositions or methods. For example, compositions that consist essentially of listed ingredients do not contain additional ingredients that would affect the properties of those compositions. Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. Weight percent, percent by weight, % by weight, wt %, and the like are synonyms that refer to the concentration of a substance as the weight of that substance divided by the weight of the composition and multiplied by 100. Percentages and ratios are by weight unless otherwise so stated.

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

This completes the description of the preferred and alternate embodiments of the invention. Those skilled in the art may recognize other equivalents to the specific embodiment described herein which equivalents are intended to be encompassed by the claims attached hereto.

What is claimed is:

1. A tagged treatment polymer, the polymer comprising a chain of chemically bonded monomeric units, at least some of the monomeric units selected from the group consisting of $G_a Q_j W_t$, $G_a\ Q_v\ W_f\ S_c$, and any combination thereof; wherein:
   the distribution of G, Q, W and S along the polymer chain are in random order and in relative amounts of a, j, t, v, f, and c;
   for polymer $G_a\ Q_v\ W_f\ S_c$ a is from about 0.001 to about 10.00 mole percent; v is from about 0 to about 97.999 mole percent; f is from about 1 to about 97.999 mole percent; c is from about 1 to about 40 mole percent; and the sum of a, v, f, and c is 100;
   for polymer $G_a Q_j W_t$ a is from about 0.001 to about 10.0 mole percent; j is from about 0 to about 99.999 mole percent; t is from about 0 to about 99.999 mole percent; and the sum of a, j, and t is 100;

G is selected from Formula I or Formula II,

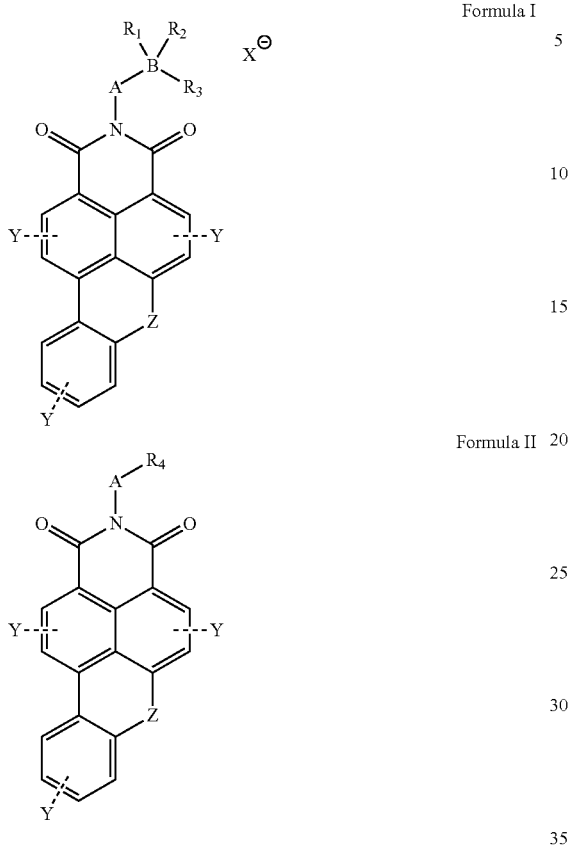

Formula I

Formula II in Formula I, each Y is selected from NO$_2$, CO$_2$H and its salts, PO$_3$H$_2$ and it salts, SO$_3$H and its salts, SO$_2$NH$_2$ or SO$_2$NR$_1$R$_2$;
Z is one of the following: CH$_2$, C═O, CR$_1$R$_2$, NH, NR$_1$, NH$_2^+$, NR$_1$R$_2^+$, NOH, O, S, SO, or SO$_2$;
R$_3$ is selected from allyl, 2-hydroxy-3-allyloxy-propyl, vinyl benzyl, 3-methacrylamidopropyl, 3-acrylamidopropyl, 2-acryloxyethyl, or 2-methacryloxyethyl;
A is absent or selected from alkyl, alkyloxyalkyl, alkylamidoalkyl, or aryl, with the proviso that when A is absent, B is nitrogen (N) and B is bonded directly to the imide nitrogen;
B is sulfur or nitrogen with the proviso that when B is sulfur only one of R$_1$ or R$_2$ is present;
X is an anionic counter ion; and
in Formula II, each Y is selected from NO$_2$, CO$_2$H and its salts, PO$_3$H$_2$ and it salts, SO$_3$H and its salts, SO$_2$NH$_2$ or SO$_2$NR$_1$R$_2$;
Z is selected from CH$_2$, C═O, CR$_2$, NH, NR$_1$, NH$_2^+$, NR$_1$R$_2^+$, NOH, O, S, SO, or SO$_2$;
A is absent or selected from alkyl, alkyloxyalkyl, alkoxy, alkylamidoalkyl, alkylamino, NH, or aryl;
R$_4$ is selected from allyl, acryl, methacryl, 2-hydroxy-3-allyloxy-propyl, vinyl benzyl, 2-acryloxyethyl or 2-methacryloxyethyl;
R$_1$ and R$_2$ are independently alkyl;
Q is selected from acrylic acid and salts thereof, methacrylic acid and salts thereof, maleic acid and salts thereof, maleic anhydride, acrylamide, crotonic acid, or acrylamidomethylpropane sulfonic acid and salts thereof; and Q cannot be the same as W;
W is selected from acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, diallylamine, acid salts of diallylamine, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, or N-vinylpyrrolidone; and
S is selected from the group consisting of sulfomethylacrylamide and sulfoethylacrylamide.

2. The polymer of claim 1, wherein G is selected from the group consisting of sulfonated-N-(3-N', N'-Dimethylaminopropyl) benzo (k,l) xanthene-3,4-dicarboxylic imide, 2-hydroxy-3-allyloxypropyl quaternary salt and sulfonated-N-(3-N', N'-Dimethylaminopropyl) benzo (k,l) xanthene-3,4-dicarboxylic imide, vinyl benzyl chloride quaternary salt, Q is acrylic acid, W is acrylamide and S is N sulfomethylacrylamide.

3. The polymer of claim 1, wherein G is selected from the group consisting of sulfonated-N-(3-N', N'-Dimethylaminopropyl) benzo (k,l) xanthene-3,4-dicarboxylic imide, 3-methacrylamidopropyl quaternary salt and sulfonated-N-(3-N', N'-Dimethylaminopropyl) benzo (k,l) xanthene-3,4-dicarboxylic imide, allyl chloride quaternary salt, Q is acrylic acid, W is acrylamide and S is N-sulfomethylacrylamide.

4. The polymer of claim 1, wherein G is sulfonated-N-(3-N', N'-Dimethylaminoethyl) benzo (k,l) xanthene-3,4-dicarboxylic imide, 3-methacrylamidopropyl quaternary salt, Q is acrylic acid, W is acrylamide and S is N-sulfomethylacrylamide.

5. The polymer of claim 1, wherein G is selected from the group consisting of sulfonated-N-(3-N', N'-Dimethylaminopropyl) benzo (k,l) xanthene-3,4-dicarboxylic imide, 3-methacrylamidopropyl quaternary salt and sulfonated-N-(3-N', N'-Dimethylaminoethyl) benzo (k,l) xanthene-3,4-dicarboxylic imide, 3-methacrylamidopropyl quaternary salt, Q is acrylic acid, W is acrylamidomethylpropane sulfonic acid.

6. The polymer of claim 1, wherein G is selected from the group consisting of sulfonated-N-(3-N', N'-Dimethylaminopropyl) benzo (k,l) xanthene-3,4-dicarboxylic imide, 2-hydroxy-3-allyloxypropyl quaternary salt and sulfonated-N-(3-N', N'-Dimethylaminopropyl) benzo (k,l) xanthene-3,4-dicarboxylic imide, vinyl benzyl chloride quaternary salt, Q is acrylic acid, W is acrylamidomethylpropane sulfonic acid.

7. The polymer of claim 1, wherein G is sulfonated-N-(3-N', N'-Dimethylaminopropyl) benzo (k,l) xanthene-3,4-dicarboxylic imide, allyl chloride quaternary salt, Q is acrylic acid, and W is acrylamidomethylpropane sulfonic acid.

8. The polymer of claim 1, wherein G is sulfonated-N-(3-N', N'-Dimethylaminopropyl) benzo (k,l) xanthene-3,4-dicarboxylic imide, vinylbenzyl chloride quaternary salt and Q is acrylic acid.

9. The polymer of claim 1, wherein G is selected from the group consisting of sulfonated-N-(3-N', N'-Dimethylaminopropyl) benzo (k,l) xanthene-3,4-dicarboxylic imide, allyl chloride quaternary salt and sulfonated-N-(3-N', N'-Dimethylaminopropyl) benzo (k,l) xanthene-3,4-dicarboxylic imide, 2-hydroxy-3-allyloxypropyl quaternary salt, and Q is acrylic acid.

10. The polymer of claim 1, wherein G is selected from the group consisting of sulfonated-N-(3-N', N'-Dimethylaminopropyl) benzo (k,l) xanthene-3,4-dicarboxylic imide, 3-methacrylamidopropyl quaternary salt and sulfonated-N-(3-N', N'-Dimethylaminoethyl) benzo (k,l) xanthene-3,4-dicarboxylic imide, 3-methacrylamidopropyl quaternary salt, and Q is acrylic acid.

11. The polymer of claim 1, wherein t is from about 0.001 to about 99.998%.

12. The polymer of claim 1, wherein Q is acrylic acid and W is acrylamide or acrylamidomethylpropane sulfonic acid.

13. The polymer of claim 1, wherein Q is acrylamide, W is acrylic acid, and S is N-sulfomethylacrylamide.

14. A fluorescent monomer selected from the group consisting of a compound of Formula I and a compound of Formula II, wherein:

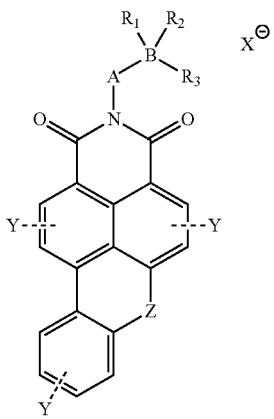

Formula I

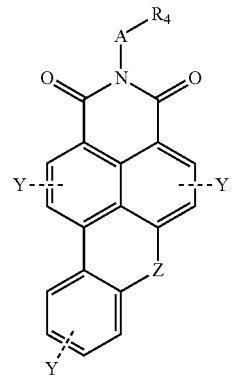

Formula II in Formula I, Y is selected from $NO_2$, $CO_2H$ and its salts, $PO_3H_2$ and it salts, $SO_3H$ and its salts, $SO_2NH_2$ or $SO_2NR_1R_2$;
Z is one of the following: $CH_2$, C=O, $CR_2$, NH, $NR_1$, $NH_2^+$, $NR_1R_2^+$, NOH, O, S, SO, or $SO_2$;
$R_3$ is selected from allyl, 2-hydroxy-3-allyloxy-propyl, vinyl benzyl, 3-methacrylamidopropyl, 3-acrylamidopropyl, 2-acryloxyethyl or 2-methacryloxyethyl;
A is absent or selected from alkyl, alkyloxyalkyl, alkylamidoalkyl, or aryl; with the proviso that when A is absent, B is nitrogen (N) and B is bonded directly to the imide nitrogen;
B is sulfur or nitrogen with the proviso that when B is sulfur only one of $R_1$ or $R_2$ is present;
X is an anionic counter ion;
in Formula II, Y is selected from $NO_2$, $CO_2H$ and its salts, $PO_3H_2$ and it salts, $SO_3H$ and its salts, $SO_2NH_2$ or $SO_2NR_2$;
Z is one of the following: $CH_2$, C=O, $CR_2$, NH, $NR_1$, $NH_2^+$, $NR_1R_2^+$, NOH, O, S, SO, or $SO_2$;
A is absent or selected from alkyl, alkyloxyalkyl, alkoxy, alkylamidoalkyl, alkylamino, NH, or aryl;
$R_4$ is selected from allyl, acryl, methacryl, 2-hydroxy-3-allyloxy-propyl, vinyl benzyl, 2-acryloxyethyl or 2-methacryloxyethyl; and
$R_1$ and $R_2$ are independently alkyl.

15. The fluorescent monomer of claim 14, wherein the fluorescent monomer is sulfonated-N-(3-N', N'-Dimethylaminopropyl) benzo (k,l) xanthene-3,4-dicarboxylic imide, 2-hydroxy-3-allyloxypropyl quaternary salt.

16. The fluorescent monomer of claim 14, wherein the fluorescent monomer is sulfonated-N-(3-N', N'-Dimethylaminopropyl) benzo (k,l) xanthene-3,4-dicarboxylic imide, vinyl benzyl chloride quaternary salt.

17. The fluorescent monomer of claim 14, wherein the fluorescent monomer is sulfonated-N-(3-N', N'-Dimethylaminopropyl) benzo (k,l) xanthene-3,4-dicarboxylic imide, allyl chloride quaternary salt.

18. The fluorescent monomer of claim 14, wherein the fluorescent monomer is sulfonated-N-(3-N', N'-Dimethylaminopropyl) benzo (k,l) xanthene-3,4-dicarboxylic imide, 3-methacrylamidopropyl quaternary salt.

19. The fluorescent monomer of claim 14, wherein the fluorescent monomer is sulfonated-N-(3-N', N'-Dimethylaminoethyl) benzo (k,l) xanthene-3,4-dicarboxylic imide, 3-methacrylamidopropyl quaternary salt.

20. A fluorescent monomer selected from sulfonated-N-(3-N', N'-Dimethylaminopropyl) benzo (k,l) xanthene-3,4-dicarboxylic imide, 2-hydroxy-3-allyloxypropyl quaternary salt; sulfonated-N-(3-N', N'-Dimethylaminopropyl) benzo (k,l) xanthene-3,4-dicarboxylic imide, vinyl benzyl chloride quaternary salt; sulfonated-N-(3-N', N'-Dimethylaminopropyl) benzo (k,l) xanthene-3,4-dicarboxylic imide, allyl chloride quaternary salt; sulfonated-N-(3-N', N'-Dimethylaminopropyl) benzo (k,l) xanthene-3,4-dicarboxylic imide, 3-methacrylamidopropyl quaternary salt; and sulfonated-N-(3-N', N'-Dimethylaminoethyl) benzo (k,l) xanthene-3,4-dicarboxylic imide, 3-methacrylamidopropyl quaternary salt.

\* \* \* \* \*